(12) United States Patent
Nakano et al.

(10) Patent No.: US 9,162,427 B2
(45) Date of Patent: Oct. 20, 2015

(54) METHOD FOR MANUFACTURING SURFACE-MODIFIED FLUORORESIN FILM, METHOD FOR MANUFACTURING RUBBER COMPOSITE, AND RUBBER PRODUCT

(75) Inventors: Hiroaki Nakano, Kobe (JP); Eiji Yao, Kobe (JP)

(73) Assignee: SUMITOMO RUBBER INDUSTRIES, LTD., Kobe-shi (JP)

( * ) Notice: Subject to any disclaimer, the term of this patent is extended or adjusted under 35 U.S.C. 154(b) by 281 days.

(21) Appl. No.: 13/643,234

(22) PCT Filed: Jun. 30, 2011

(86) PCT No.: PCT/JP2011/064996
§ 371 (c)(1),
(2), (4) Date: Oct. 24, 2012

(87) PCT Pub. No.: WO2012/017758
PCT Pub. Date: Feb. 9, 2012

(65) Prior Publication Data
US 2013/0040156 A1    Feb. 14, 2013

(30) Foreign Application Priority Data

Aug. 4, 2010 (JP) .................. 2010-175414

(51) Int. Cl.
*B29C 59/16* (2006.01)
*B32B 25/08* (2006.01)
(Continued)

(52) U.S. Cl.
CPC .............. *B32B 25/08* (2013.01); *B29C 59/16* (2013.01); *B32B 27/16* (2013.01); *B32B 27/322* (2013.01); *C08J 3/28* (2013.01); *C08J 7/123* (2013.01);
(Continued)

(58) Field of Classification Search
None
See application file for complete search history.

(56) References Cited

U.S. PATENT DOCUMENTS 4,064,030 A * 12/1977 Nakai et al. .............. 204/192.36
4,397,903 A *  8/1983 Allen et al. ................... 428/156
(Continued)

FOREIGN PATENT DOCUMENTS

| DE | 19954335 A1 | 5/2000 |
|---|---|---|
| JP | 7-33890 A | 2/1995 |

(Continued)

OTHER PUBLICATIONS

International Search Report for International Application No. PCT/JP2011/064996 dated Aug. 9, 2011.
(Continued)

*Primary Examiner* — Ramsey Zacharia
(74) *Attorney, Agent, or Firm* — Birch Stewart Kolasch & Birch, LLP

(57) ABSTRACT

There are provided a method for manufacturing a surface-modified fluororesin film capable of long-term inventory storage, a method for manufacturing a rubber composite composed of the surface-modified fluororesin film and rubber bonded together, and a rubber product for medical use made of the rubber composite. The method for manufacturing a surface-modified fluororesin film comprises the step of performing surface roughening on a fluororesin film RF by applying an ion beam from an anode layer ion source to the surface of the fluororesin film RF. A rubber is placed over the roughened surface of the thusly produced surface-modified fluororesin film, and, through vulcanization molding process, the surface-modified fluororesin film and the tuber can be firmly bonded to each other.

4 Claims, 9 Drawing Sheets

(51) Int. Cl.
  *C08F 14/18* (2006.01)
  *C08J 3/28* (2006.01)
  *B32B 27/16* (2006.01)
  *B32B 27/32* (2006.01)
  *C08J 7/12* (2006.01)

(52) U.S. Cl.
  CPC ...... *C08J 2327/12* (2013.01); *Y10T 428/31826* (2015.04); *Y10T 428/31837* (2015.04)

(56) References Cited

U.S. PATENT DOCUMENTS

| | | |
|---|---|---|
| 5,425,832 A | 6/1995 | Kusano et al. |
| 5,965,629 A | 10/1999 | Jung et al. |
| 6,432,510 B1 | 8/2002 | Kim et al. |

FOREIGN PATENT DOCUMENTS

| | | |
|---|---|---|
| JP | 2000-143850 A | 5/2000 |
| JP | 2008-174791 A | 7/2008 |
| JP | 2009-263529 A | 11/2009 |

OTHER PUBLICATIONS

Sasaki et al., "Linear Ion Gen no. Kaihatsu," ULVAC Technical Journal, 2005, vol. 63, pp. 26-29 with 6 pages of English translation.
Lackner et al., "Polymer Pre-Treatment by Linear Anode Layer Source Plasma for Adhesion Improvement of Sputtered TiN Coatings", Vacuum, 83, 2009, pp. 302-307.

* cited by examiner

METHOD FOR MANUFACTURING SURFACE-MODIFIED FLUORORESIN FILM, METHOD FOR MANUFACTURING RUBBER COMPOSITE, AND RUBBER PRODUCT

TECHNICAL FIELD

The present invention relates to a surface-modified fluororesin film, a rubber composite formed by bonding the fluororesin film and rubber together, and a medical rubber product made of the rubber composite.

BACKGROUND ART

Fluorine resin has a number of features including excellence in chemical stability and thermal stability, and a low coefficient of friction attributable to its self-lubricating nature. However, fluorine resin is very costly compared to other resins for general purpose use, and the expensiveness has limited its uses in spite of the superior characteristics.

Furthermore, while fluorine resin exhibits chemical stability, contrarily it has presented difficulties in laminating a sheet- or film-shaped fluorine resin to a different material by an adhesive with the aim of reducing the amount of use. This has precluded the use of fluorine resin in applications for which the chemical stability can be exploited, for example, a stopper of a medicament container.

With this in view, as an attempt to render fluorine resin adherable to a different raw material by an adhesive, there is proposed a technique for improving an affinity for water, or hydrophilicity at the surface of a molded body of fluorine resin by performing surface roughening treatment on the molded body through plasma irradiation and substituting implanted plasma ion atoms for fluorine atoms of the surface of the molded body (refer to Patent literature 1).

PRIOR ART REFERENCE

Patent Literature

Patent literature 1: Japanese Unexamined Patent Publication JP-A 2009-263529

SUMMARY OF THE INVENTION

Problems to be Solved by the Invention

However, it is known that such a technique as disclosed in Patent literature 1 whereby to obtain hydrophilicity by substituting different atoms for inert surface atoms through plasma treatment poses the problem of molecular migration from the treated (modified) surface to the interior of resin due to thermal fluctuation of polymer, and also poses the problem of uncertainty about the permanence of surface-modification effect (surface hydrophilicity) due to negative factors such as liberation of resultant hydrophilic low-molecular substances.

In light of a gradual reduction in surface-modification effect over time, the use (inventory storage) of a fluorine resin-based molded body whose surface had been modified by the technique disclosed in Patent literature 1 is limited to a short period of time. If the volume of production of articles using the fluorine resin-based molded bodies as materials in a succeeding manufacturing operation is cut down according to erroneous demand forecast, the fluorine resin-based molded bodies carried in stock may be rejected as nonconforming (defective) materials.

The present invention has been devised in view of the problems as mentioned supra, and accordingly its object is to provide a method for manufacturing a surface-modified fluororesin film capable of long-term inventory storage, a method for manufacturing a rubber composite composed of the surface-modified fluororesin film and rubber bonded together, and a rubber product for medical use made of the rubber composite.

Means for Solving the Problem

The method for manufacturing a surface-modified fluororesin film pursuant to the present invention comprises a step of performing surface roughening on a fluororesin film by applying an ion beam from an anode layer ion source to a surface of the fluororesin film.

It is preferable that an irradiation voltage for generating an ion beam is adjusted to be greater than or equal to 1.5 kV in the anode layer ion source.

The fluororesin film is made of any one of PTFE, denatured PTFE, PFA, and ETFE.

PTFE, exhibiting high resistance to heat and having the lowest coefficient of friction, is used in the manufacture of a rubber composite used for that part of a product which is subjected to high temperature and a rubber composite used for a sliding part of a product.

Denatured PTFE, being analogous in physical properties to PTFE and exhibiting good moldability, is suitable for the manufacture of a rubber composite having a complicated shape.

PFA and ETFE, being capable of formation of a smooth sheet, is suitable for the manufacture of a rubber composite which needs to be designed to have surface smoothness.

The method for manufacturing a rubber composite pursuant to the present invention comprises a step of performing surface roughening on a fluororesin film by applying an ion beam from an anode layer ion source to a surface of the fluororesin film and a step of placing a rubber over the surface of the fluororesin film and bonding them together by means of vulcanization molding.

The rubber product for medical use pursuant to the present invention comprises a fluororesin film and rubber. The fluororesin film has its surface roughened by irradiation of an ion beam from an anode layer ion source, and the rubber is placed over the roughened surface of the fluororesin film. Through vulcanization molding process, the rubber finds its way into the roughened surface of the fluororesin film so as to adhere tightly to the fluororesin film under an anchor effect.

Advantages of the Invention

The present invention allows the provision of a method for manufacturing a surface-modified fluororesin film capable of long-term inventory storage, a method for manufacturing a rubber composite composed of the surface-modified fluororesin film and rubber bonded together, and a rubber product for medical use made of the rubber composite.

MODES FOR CARRYING OUT THE INVENTION

Figure 1:
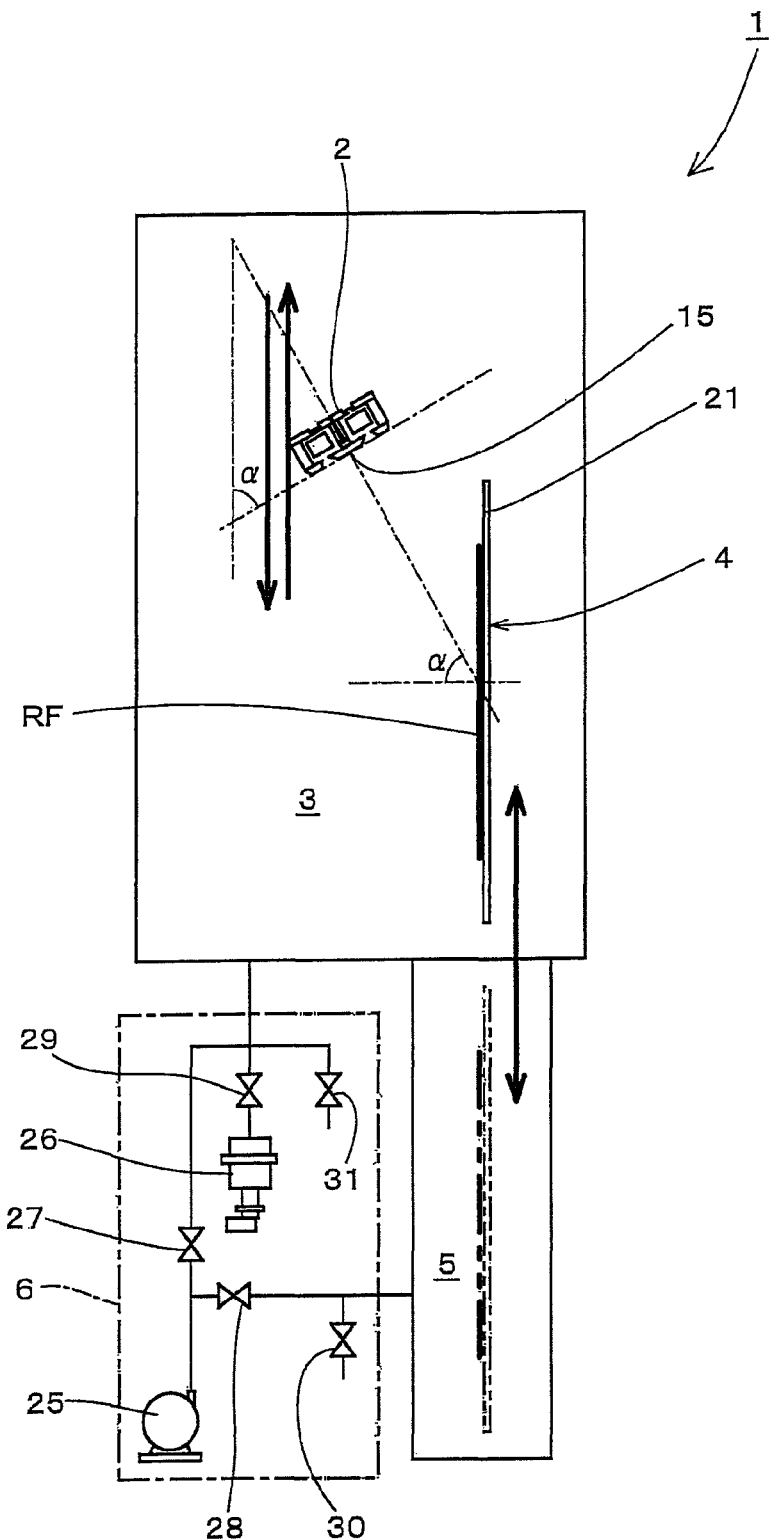
FIG. 1 is a schematic diagram of a surface-modifying apparatus.
Figure 2:
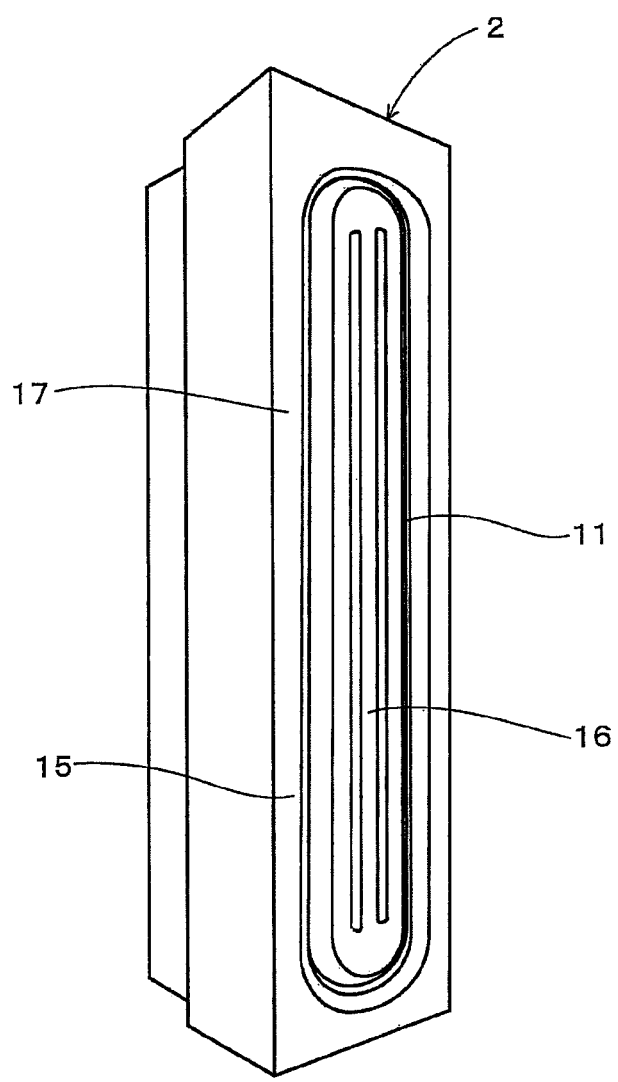
FIG. 2 is an external view of an ion irradiator.
Figure 3:
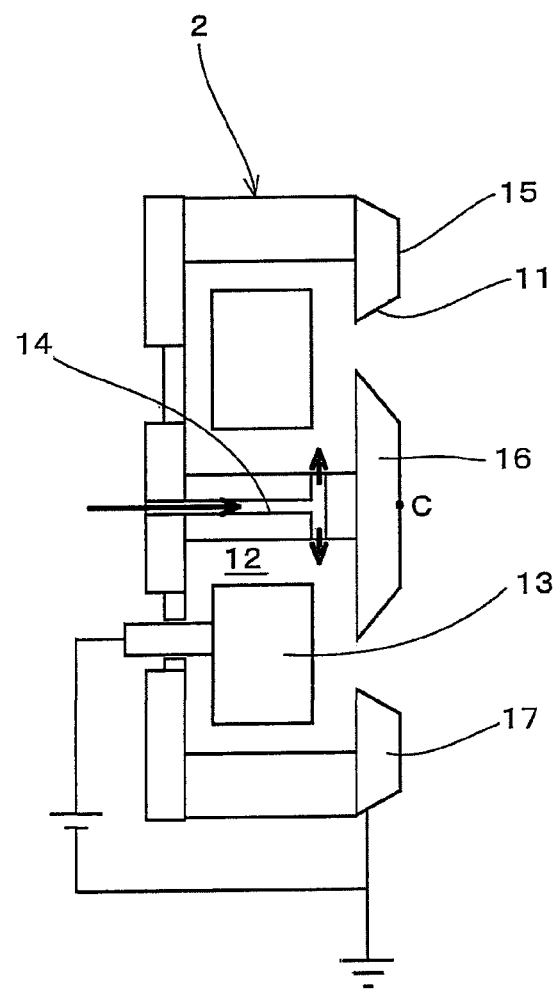
FIG. 3 is a sectional view of the ion irradiator taken along a direction perpendicular to the direction of the length thereof.

FIG. 1 is a schematic diagram of a surface-modifying apparatus 1, FIG. 2 is an external view of an ion irradiator 2, and FIG. 3 is a sectional view of the ion irradiator 2 taken along a direction perpendicular to the direction of the length thereof.

The surface-modifying apparatus 1 is adapted to modify the surface of a fluororesin film RF constituting a rubber composite.

The surface-modifying apparatus 1 is composed of a treatment chamber 3, the ion irradiator 2, an ion irradiator moving device, a retainer 4, a front chamber 5, and a vacuum device 6.

The treatment chamber 3 is a hermetically sealable room for accommodating the ion irradiator 2, the ion irradiator moving device, and the retainer 4.

The ion irradiator 2, which is in the general form of a slim rectangular prism, comprises a slit 11, a space 12, an anode 13, and a gas flow channel 14. The ion irradiator 2 is an anode layer ion source constructed by making improvements to an anode layer-type Hall thruster.

The slit 11 is a loop-like slot formed at one narrow elongated surface 15 (hereafter termed "irradiation side surface 15") of the ion irradiator 2, the opposed shorter sides of which are each curved in an arcuate form, and the opposed longer sides of which are each defined by a straight line. In the irradiation side surface 15-forming region, a part lying inside the slit 11 is referred to as an inner pole 16, and a part lying outside the slit 11 is referred to as an outer pole 17.

In the ion irradiator 2, a ferromagnetic substance is used for at least the material constituting the irradiation side surface 15. A built-in permanent magnet of the ion irradiator 2 imparts South magnetic polarity to the inner pole 16, and imparts North magnetic polarity to the outer pole 17.

The space 12 formed within the ion irradiator 2 is a loop-like hollow cavity which corresponds in shape to the slit 11 yet is larger in width than the slit 11. The slit 11 allows communication between the space 12 and the exterior thereof.

The anode 13 is a loop-like electrode housed in the loop-like space 12. The anode 13 is made of copper or an alloy of copper.

The gas flow channel 14 is a path for admitting a gas serving as an ion source from outside the ion irradiator 2 into the space 12.

In the ion irradiator 2, the outer pole 17 is grounded (earthed), and the anode 13 is connected to a DC power source.

In the ion irradiator 2, the irradiation side surface 15-forming region (may hereafter be abbreviated as "irradiation side surface 15") is grounded, and a voltage is impressed between it and the anode 13. Moreover, in the ion irradiator 2, with the inner pole 16 acting as a South magnetic pole and the outer pole 17 acting as a North magnetic pole, a magnetic field is formed substantially perpendicularly to an axial electric field at the opening part of the slit 11.

In the vicinity of the slit 11 at the loop-like space 12 of the ion irradiator 2, a gas supplied from the gas flow channel 14 is ionized in the form of plasma by electrons which are transferred between the irradiation side surface 15 and the anode 13. The resultant electrons move toward the irradiation side surface 15, and the ions are accelerated by a thin layer (anode layer) between the anode 13 and the slit 11 so as to be discharged to the outside through the slit 11.

The ion irradiator moving device is provided to move the ion irradiator 2 reciprocally in a horizontal direction. The ion irradiator moving device holds the ion irradiator 2 in a manner such that the direction of length, or lengthwise direction of the ion irradiator 2 is perpendicular to the horizontal direction (the lengthwise direction coincides with a vertical direction). The ion irradiator moving device is so designed that an angle α between the irradiation side surface 15 of the ion irradiator 2 and the direction of travel can be changed freely insofar as it falls within the range of 0 to 90 degrees. The ion irradiator moving device can be operated under varying travel conditions; that is, for example, the rate of reciprocation, resting time at each of the limit of forward travel and the limit of return travel, and the number of travel (forward motion and return motion are counted separately as one travel) can be changed on an as needed basis. The ion irradiator moving device can be configured to move the ion irradiator 2 either in the vertical direction or in any direction other than the horizontal and vertical directions.

The retainer 4 is a device for holding the fluororesin film RF which is to be subjected to modification treatment. The retainer 4 comprises a thick, sturdy rectangular glass substrate 21. The glass substrate 21 is incorporated in the retainer 4, with its surface kept in alignment with the vertical direction.

The retainer 4 is mounted so as to be freely brought to a rest at positions so that the distance between the surface of the glass substrate 21 and the ion irradiator 2 in a direction perpendicular to the direction of reciprocation remains invariant regardless of the location of the ion irradiator 2 in reciprocating motion. As will hereafter be described, the retainer 4 is mounted for travel between the treatment chamber 3 and the front chamber 5, and it is for this reason that the retainer 4 is described as being freely brought to a rest.

The front chamber 5 is a hermetically sealable room for accommodating the retainer 4. The front chamber 5 is continuous with the treatment chamber 3, yet is separable from the treatment chamber 3 by a gate which can be opened and closed under remote control. The front chamber 5 is so designed that the retainer 4 can be moved between it and the treatment chamber 3, and the movement of the retainer 4 between the front chamber 5 and the treatment chamber 3 is effected by teleoperation while opening and closing the gate acting as a partition between the front chamber 5 and the treatment chamber 3.

The vacuum device 6 is composed of a pre-vacuum pump 25, a post-vacuum pump 26, and a plurality of automatic valves 27, 28, 29, 30, and 31.

The pre-vacuum pump 25 is a so-called roughing vacuum pump which is operated at a low degree of vacuum. An oil-sealed rotary vacuum pump is used for the pre-vacuum pump 25. The pre-vacuum pump 25 is connected, through the automatic valves 27 and 28, to the treatment chamber 3 and the front chamber 5.

The post-vacuum pump 26 is a vacuum pump which is operated for acquisition of a high degree of vacuum. A cryogenic pump is used for the post-vacuum pump 26. The post-vacuum pump 26 is connected, through the automatic valve 29, to the treatment chamber 3.

The automatic valve 30 is a leak valve for releasing the vacuum of the front chamber 5, and the automatic valve 31 is a leak valve for releasing the vacuum of the treatment chamber 3.

Next, a description will be given as to surface-modifying treatment which is performed on the fluororesin film RF by the surface-modifying apparatus 1.

Figure 4:
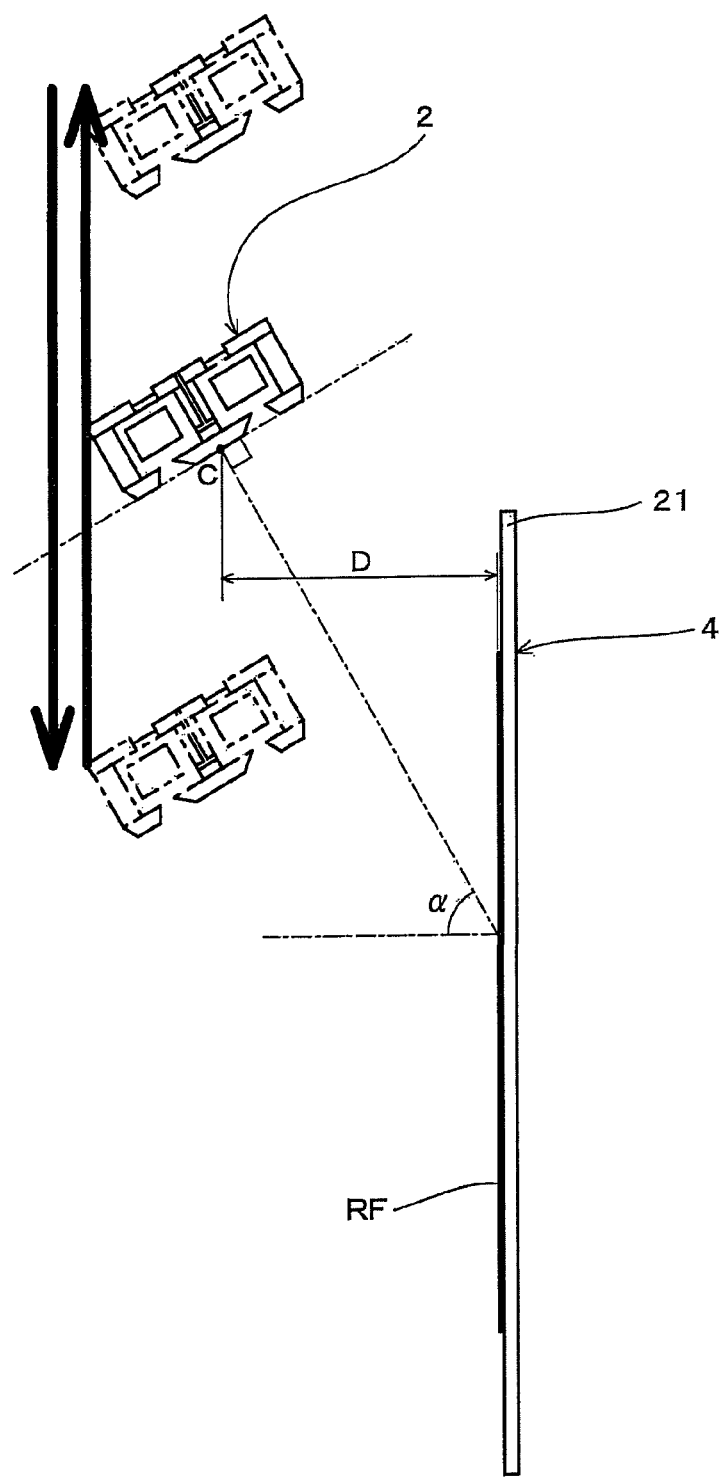
FIG. 4 is a view showing a state of ion beam irradiation effected by the ion irradiator.

FIG. 4 is a view showing a state of ion beam irradiation effected by the ion irradiator 2.

The first step is to set the fluororesin film RF which is to be subjected to modification treatment in position on the glass substrate 21 of the retainer 4. PTFE (polytetrafluoroethylene), denatured PTFE (copolymer of monomer 4F and a trace amount of perfluoro alkoxide), PFA (copolymer of tetrafluoroethylene and perfluoroalkyl vinyl ether), and ETFE (copolymer of tetrafluoroethylene and ethylene) can be used for the film-shaped fluororesin. Moreover, the film has preferably a thickness in a 10 μm- to 150 μm range.

The fluororesin film RF is cut in a rectangular shape, and the four corners or two opposed sides thereof are directly or indirectly secured to the glass substrate 21. The fluororesin film RF is tensioned slightly to an extent that would prevent development of wrinkles.

Referring to FIG. 1, the glass substrate 21 with the fluororesin film RF secured on it becomes integral with the retainer 4 within the front chamber 5.

The front chamber 5 and the treatment chamber 3 are hermetically sealed to be cut off from the outside environment. The gate acting as a partition between the front chamber 5 and the treatment chamber 3 is opened.

With the automatic valves 27 and 28 left opened and the automatic valves 29, 30, and 31 left closed, the pre-vacuum pump 25 of the vacuum device 6 is actuated to depressurize the front chamber 5 and the treatment chamber 3.

Upon the degree of vacuum in the front chamber 5 and the treatment chamber 3 reaching a predetermined level, for example, $10^2$ Pa, then the retainer 4 is moved from the front chamber 5 to the treatment chamber 3, and the gate acting as a partition between the front chamber 5 and the treatment chamber 3 is closed.

The fluororesin film RF, now existing within the treatment chamber 3, is disposed in an appropriate position in accordance with the distance to the ion irradiator 2 and an angle for ion irradiation α. As employed herein the ion irradiation angle α refers to the angle which the direction in which an ion beam is applied to a modification target (fluororesin film RF) forms with a direction perpendicular to a to-be-modified surface. In the surface-modifying apparatus 1, the ion irradiation angle α takes on the same value as the angle α between the irradiation side surface 15 and the direction of travel of the ion irradiator moving device.

Moreover, the fluororesin film RF is secured to the glass substrate 21, with any one of its two opposed-side pairs kept in alignment with the direction of the length of the ion irradiator 2.

Subsequently, upon the closure of the automatic valves 27 and 28 and the opening of the automatic valve 29, the pre-vacuum pump 25 comes to a halt, whereas the post-vacuum pump 26 is actuated. The treatment chamber 3 is depressurized by the post-vacuum pump 26 until the degree of vacuum reaches an even higher level, for example, $10^{-2}$ Pa.

The ion irradiator 2 is attached to the ion irradiator moving device in a manner such that the angle α between the irradiation side surface 15 and the direction of travel of the ion irradiator moving device takes on a predetermined value. An ionizable gas is fed to the ion irradiator 2 from the gas flow channel 14 at a predetermined flow rate. Preferred examples of the ionizable gas include an argon gas, an oxygen gas, and a nitrogen gas. These gases can be used singly, or two or more of them can be used in combination. In particular, an argon gas is desirable for use, because it is less likely to form a chemically active functional group.

After the degree of vacuum in the treatment chamber 3 has settled into the predetermined value, the ion irradiator 2 is actuated for application of an ion beam to the fluororesin film RF to start surface modification. Moreover, the ion irradiator 2 is moved from one of the limits of horizontal travel, or one travel limit toward the other one of the limits of horizontal travel, or the other travel limit, at a predetermined rate of travel by the ion irradiator moving device.

Following the completion of a predetermined number of travels of the ion irradiator 2 from one travel limit to the other travel limit and vice versa, the ion irradiator 2 ceases from travel and its operation comes to an end. Thus, surface modification is finished. The surface modification thusly conducted is a process to roughen the surface of the fluororesin film RF by breaking the internal molecular structure of the surface and nearby regions of the fluororesin film RF under the irradiation of ion beams.

The surface-modified fluororesin film RF is laminated on a yet-to-be-vulcanized rubber sheet or the like blended with a cross-linking agent, and the resultant layered body is molded into a rubber composite of a predetermined shape by a vulcanization molding technique using a mold. Having been modified (roughened) at its surface, the fluororesin film RF is caused to adhere tightly to the rubber by the vulcanization molding technique without the necessity of using an adhesive or the like. This tight adherence can be achieved by an anchor effect resulting from a phenomenon in which the vulcanized rubber finds its way into the roughened surface of the fluororesin film RF.

Exemplary of the rubber used as a raw material for the rubber composite are: butyl-based rubber; isoprene rubber; butadiene rubber; styrene butadiene rubber; natural rubber; chloroprene rubber; nitrile-based rubber such as acrylonitrile butadiene rubber; nitrile hydroxide-based rubber; norbornene rubber; ethylene propylene rubber; ethylene-propylene-diene rubber; acrylic rubber; ethylene-acrylate rubber; fluorine-containing rubber; chlorosulfonated polyethylene rubber; epichlorohydrin rubber; silicone rubber; urethane rubber; polysulfide rubber; phosphazene rubber; and 1,2-polybutadiene.

Those rubber materials can be used singly, or two or more of them can be used in combination.

Although the material used for the rubber composite is not limited to the foregoing, it is desirable to use butyl-based rubber or/and ethylene-propylene-diene rubber (hereafter referred to simply as "EPDM rubber").

The desirability of butyl-based rubber resides in its excellence in resistance to gas permeation and resistance to water vapor permeation.

As butyl-based rubber, although a heretofore known compound can be used, for example, isobutylene-isoprene copolymer rubber, halogenated isobutylene-isoprene copolymer rubber (hereafter referred to as "halogenated butyl rubber"), or a denatured product thereof can be used. Examples of the denatured product include a brominated compound of isobutylene-p-methylstyrene copolymer. Among them, halogenated butyl rubber is desirable for use because of its readiness to form cross-linkage, and the use of chlorinated butyl rubber or brominated butyl rubber is particularly desirable.

On the other hand, the desirability of EPDM rubber resides in its excellence in workability. Although EPDM rubber falls into two categories, namely non-oil extended-type EPDM rubber composed solely of rubber components and oil extended-type EPDM rubber including extender oil in addition to rubber components, either one will do in the present invention. Examples of diene monomer for constituting EPDM rubber include dicyclopentadiene, methylene norbornene, ethylidenenorbornene, 1,4-hexadiene, and cyclo octadiene.

Further, halogenated butyl rubber and EPDM rubber are compatible with each other and can therefore be preferably used in combination. The desirability of the combination resides in its excellence in resistance to gas permeation and resistance to water vapor permeation, and also its workability.

In a case where the rubber composite finds application in a medical rubber product such as a gasket for a syringe, butyl rubber is desirable for use as a major rubber constituent because of its low permeability to gas. As the cross-linking agent, the use of a triazine derivative is desirable from a cleanliness viewpoint.

Where the technique of accomplishing vulcanization adhesion between the fluororesin film RF and rubber is concerned, the fluororesin film RF and the rubber in contact state are subjected to heat and pressure for a predetermined period of time, so that the rubber is caused to adhere to the fluororesin film RF while effecting cross-linking. The time and temperature for vulcanization adhesion are determined with consideration given to the necessity for cross-linking on an uncrosslinked rubber composition. In the above-described vulcanization adhesion, basically an adhesive is not used, wherefore the time and temperature for vulcanization adhesion are determined on the basis of rubber composition (there is no need to regard adhesive properties such as heat resistance). A typical rubber composition is vulcanized at from 140 deg. C. to 200 deg. C. While the time required for cross-linking is dependent upon the dimension of a molded body, for example, in the case of forming a small item such as a rubber stopper for medical use, the cross-linking time falls within the range of about 1 minute to 20 minutes. In the application of pressure for vulcanization adhesion, a pressure level such as set for a heretofore known rubber cross-linking method is adopted. In general, a pressure is advisably applied to a female mold adapted for the molded body to such an extent that rubber can be charged completely into the mold without causing any clearance. In the case of forming a small item such as a rubber stopper for medical use, the level of pressure stands at about 20 MPa.

TABLE 1

| | | Film raw material | Irradiation voltage (kV) | Ionizable gas | Gas flow rate (ccm/min.) | Ion irradiation angle α (degrees) | Rate of travel (mm/sec.) | Number of travel | Discoloration | Peel strength (N/mm) Immediately afterward | Peel strength (N/mm) After 360 days | Evaluation |
|---|---|---|---|---|---|---|---|---|---|---|---|---|
| Practical example | 1 | PTFE | 1.5 | Argon | 40 | 60 | 20 | 1 | Not found | 1.9 | — | Good |
| | 2 | PTFE | 2.5 | Argon | 40 | 60 | 20 | 1 | Not found | 2.5< | — | Good |
| | 3 | PTFE | 3.5 | Argon | 40 | 60 | 20 | 1 | Not found | 2.5< | — | Good |
| | 4 | PTFE | 1.5 | Argon | 40 | 60 | 10 | 1 | Not found | 2.2 | — | Good |
| | 5 | PTFE | 1.5 | Argon | 40 | 60 | 40 | 1 | Not found | 1.5 | — | Good |
| | 6 | PTFE | 1.5 | Argon | 40 | 60 | 20 | 4 | Not found | 2.5< | — | Good |
| | 7 | PTFE | 2.5 | Oxygen | 40 | 60 | 20 | 1 | Not found | 2.5< | — | Good |
| | 8 | PTFE | 2.5 | Nitrogen | 40 | 60 | 20 | 1 | Not found | 2.5< | — | Good |
| | 9 | PTFE | 2.5 | Argon, Oxygen | 40 | 60 | 20 | 1 | Not found | 2.5< | — | Good |
| | 10 | Denatured PTFE | 2.5 | Argon | 40 | 60 | 20 | 1 | Not found | 2.5< | — | Good |
| | 11 | PFA | 2.5 | Argon | 40 | 60 | 20 | 1 | Not found | 2.5< | — | Good |
| | 12 | ETFE | 1.5 | Argon | 40 | 60 | 20 | 1 | Not found | 2.5< | — | Good |
| | 13 | PTFE | 2.5 | Argon | 40 | 30 | 20 | 1 | Not found | 2.5< | — | Good |
| | 14 | PTFE | 2.5 | Argon | 60 | 60 | 20 | 1 | Not found | 2.5< | — | Good |
| | 15 | PTFE | 2.5 | Argon | 40 | 60 | 10 | 1 | Not found | 2.5< | 2.5< | Good |
| | 16 | Denatured PTFE | 2.5 | Argon | 40 | 60 | 10 | 1 | Not found | 2.5< | 2.5< | Good |
| Comparative example | 1 | PTFE | 1.0 | Argon | 40 | 60 | 20 | 1 | Not found | 0.1 | — | Poor |
| | 2 | PTFE | 1.0 | Argon | 40 | 60 | 10 | 4 | Not found | 0.6 | — | Poor |
| | 3 | PTFE | 4.5 | Argon | 40 | 60 | 20 | 1 | — | — | — | Poor |
| | 4 | PTFE | 2.5 | Argon | 40 | 60 | 10 | 12 | Found | 2.3 | — | Poor |
| | 5 | PTFE | — | — | — | — | — | — | — | 0.1 | — | Poor |

Remark 1: [2.5<] in "Peel strength" column stands for peel strength as measured upon interruption of peel-strength measurement due to rubber layer rupture Remark 2: Absence of results on "Discoloration", "Peel strength" in Comparative example 3 ascribable to suspension of operation with reduction in vacuum level caused by resin-degrading gas during ion-beam irradiation Remark 3: No surface modification conducted in Comparative example 5

Table 1 show conditions under which the fluororesin film RF is modified at its surface by the surface-modifying apparatus 1, and the result of evaluation on the surface-modified fluororesin film RF. The term "peel strength" listed in Table 1 refers to peel strength as observed between the fluororesin film RF and a rubber sheet bonded to each other through vulcanization adhesion. The designation "2.5<" in the peel-strength column of Table 1 stands for peel strength as measured upon the interruption of peel strength measurement due to rupture of a rubber sheet that occurred during friction tests.

The following are conditions common to surface modification and vulcanization adhesion.
(1) Ion irradiator: IZOVAC BEAM CLEANING SYSTEM (anode layer ion source) manufactured by IZOVAC Ltd. The ion irradiator is driven by a driving apparatus manufactured by LAN TECHNICAL SERVICE Co., Ltd.

(2) Preset vacuum: $10^{-2}$ Pa
(3) Fluororesin film: VALFRON (registered trademark) manufactured by NIPPON VALQUA INDUSTRIES, LTD. used as PTFE, the thickness of which is 100 μm; NEW VALFRON EX1 (VALFRON is registered trademark) manufactured by NIPPON VALQUA INDUSTRIES, LTD. used as denatured PTFE, the thickness of which is 100 μm; Neoflon PFA film (Neoflon is registered trademark) manufactured by DAIKIN INDUSTRIES. LTD. used as PFA, the thickness of which is 100 μm; and FluonETFE (registered trademark) manufactured by ASAHI GLASS. CO., LTD. used as ETFE, the thickness of which is 100 μm
(4) Distance between Ion irradiator and Fluororesin film: 100 mm in terms of the distance from a widthwise central point of the irradiation side surface 15 (indicated by symbol C in FIGS. 3 and 4) to the fluororesin film in a direction perpendicular to the direction of travel of the ion irradiator 2 (indicated by symbol D in FIG. 4)
(5) Unvulcanized rubber sheet: 2 mm-thick halogenated butyl rubber
(6) Cross-linking agent: 2-Di-n-butylamino-4,6-dimercapto-s-triazine manufactured by SANKYO KASEI CO., LTD. under the name of Zisnet DB (registered trademark)
(7) Conditions for vulcanization adhesion: Temperature of 180 deg. C.; Treatment time of 5 minutes; and Treatment pressure of 20 MPa In Table 1, "Irradiation voltage" refers to DC voltage which is impressed between the anode 13 and the irradiation side surface 15, "Rate of travel" refers to the rate at which the ion irradiator 2 travels as seen in FIG. 1, and "Number of travel" refers to the number of times the ion irradiator 2 travels on the assumption that one-way movement is counted as one travel.

The presence or absence of discoloration as listed in Table 1 has been examined by visually checking the surface-modified fluororesin film.

In the determination of peel strength, a rubber composite obtained as the result of vulcanization adhesion was cut into 20 mm-wide rectangular strips, and the strip was held at its lengthwise one end in a manner such that the fluororesin film and the rubber are caught by separate upper and lower chucks, respectively. In this state, one side of the strip has been moved upward at a rate of 50 mm/min, and the resistive force acting on it was determined by measurement.

Figure 5:
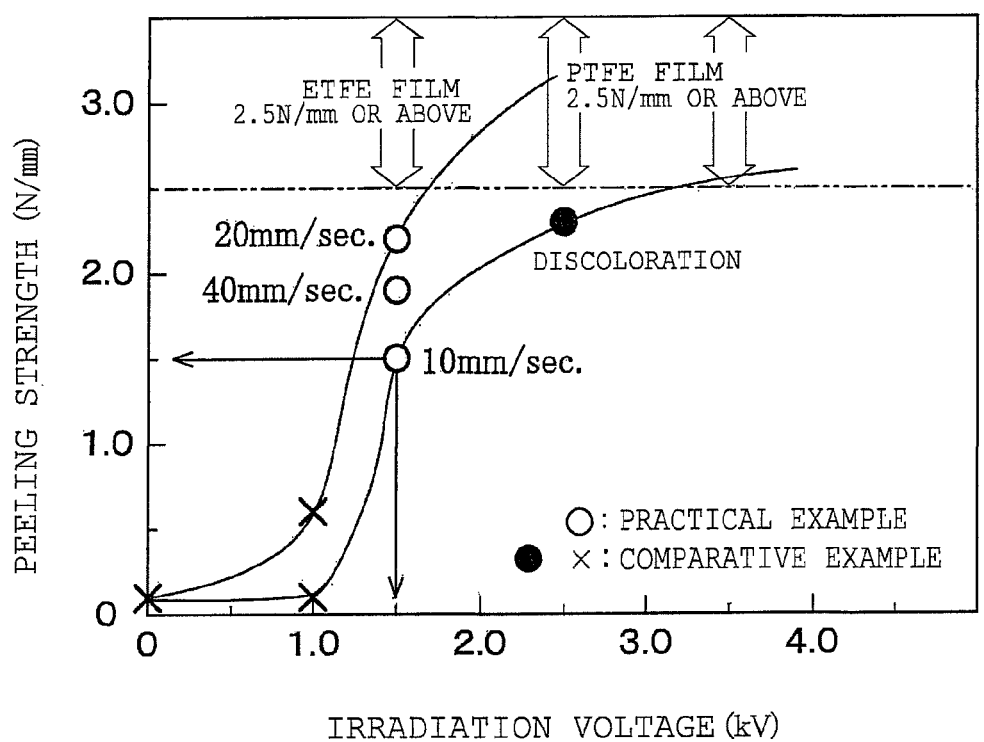
FIG. 5 is a chart indicating the influence of irradiation voltage on peel strength.
Figure 6:
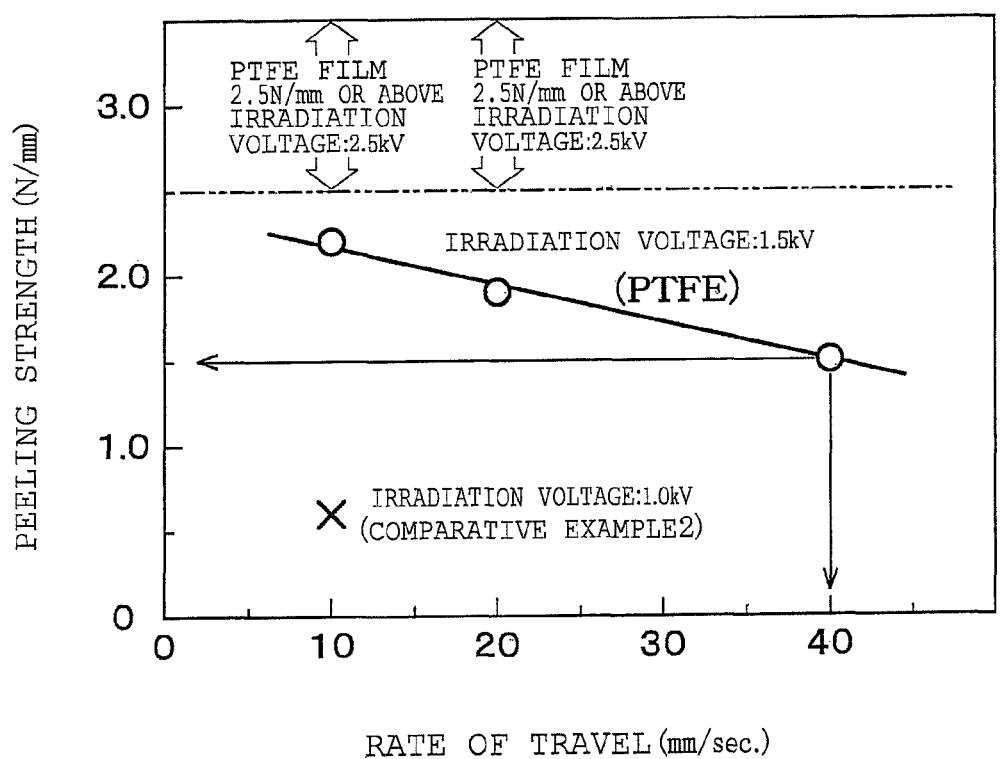
FIG. 6 is a chart indicating the influence of the rate of travel on peel strength in a case where irradiation voltage stands at 1.5 kV.

FIG. 5 is a chart indicating findings about the influence of irradiation voltage on peel strength according to the evaluation result listed in Table 1, and FIG. 6 is a chart indicating findings about the influence of the rate of travel on peel strength in the case where the irradiation voltage stands at 1.5 kV according to the evaluation result listed in Table 1.

As will be seen in FIG. 5, by adjusting the irradiation voltage to be greater than or equal to 1.5 kV, it is possible to impart practically sufficient strength, specifically a peel strength of greater than or equal to 1.5 N/mm, to the rubber composite.

It will also be seen from FIG. 6 that, the lower is the rate of travel, the higher is the peel strength of the rubber composite. In the case where the irradiation voltage of the ion irradiator 2 is set at 1.5 kV, by adjusting the rate of travel to be lower than or equal to 40 mm/sec., it is possible to impart a peel strength of greater than or equal to 1.5 N/mm to the PTFE film (fluororesin film). However, the data on Comparative example 2 indicates that a sufficiently high peel strength cannot be obtained in the case where the irradiation voltage stands at a low level in spite of a decrease of the rate of travel and an increase of the number of travel to several times.

Furthermore, as will be seen from the data on Comparative example 4 listed in Table 1, when effecting surface modification under undue conditions (unduly low rate of travel, unduly large number of travel), discoloration occurs in the surface-modified fluororesin film.

As will be seen from the data on Practical examples 2 and 14 and the data on Practical example 13 listed in Table 1, although the ion irradiation angle α was set differently for Practical example 2, 14 and Practical example 13, namely 60 degrees and 30 degrees, respectively, there is no appreciable difference between them. The surface modification effect produced by ion beams is dependent on the relationship between the ion irradiation angle α and the crystalline structure (atomic structure) of a modification target, and it is thus desirable to render the ion irradiation angle α different from the direction of atomic arrangement. In the above-described fluororesin film, by adjusting the ion irradiation angle α to fall at least within the range of 30 degrees to 60 degrees, it is possible to accomplish satisfactory surface modification (surface roughening).

The surface-modified fluororesin film implemented as Practical example 3 has been examined in respect of the composition of the modified surface by means of ESCA (Electron Spectroscopy for Chemical Analysis). The result showed that the surface has a composition of 56% F (fluorine), 41% C (carbon), 2.4% O (oxygen), and 0.1% N (nitrogen). As compared with the theoretical composition of PTFE, namely 66.6% F and 33.3% C, a decrease of the percentage of F and the presence of other elements such as O and N have been confirmed. Presumably, fluorine atoms existing at the uppermost surface part have been removed, and O and N that are deemed to be air-derived elements have been incorporated in a minor amount.

The surface shape of the surface-modified fluororesin film implemented as Practical example 3 has been observed by SPM (Scanning-type probe microscope). The result showed that there was an increase in projected area ratio. More specifically, the projected area ratio prior to surface modification was 1.6%, whereas the projected area ratio subsequent to surface modification was 15.9%. In addition to that, according to the result of observation of SPM images and the result of SEM (Scanning-type electron microscope) observation, minute surface asperities were found after surface modification, and this resulted in an increase in surface area. The increase in surface area and the presence of surface asperities are conducive to enhancement in vulcanization adhesion strength.

In order to verify the stability of modification effect after surface modification treatment, the surface-modified fluororesin films have been stored at constant temperature and humidity (temperature of 23 deg. C., humidity of 55%) in an air atmosphere, and changes in the surface elements of the fluororesin films in storage were checked every 30 days by means of ESCA. Moreover, after a period of storage, the fluororesin films were each bonded to a rubber sheet through vulcanization adhesion for peel strength measurement. The measurement result showed that there were no signs of deterioration in peel strength and change in element composition in the surface-modified fluororesin film, which had been stored for about a year, and the rubber bonded to each other through vulcanization adhesion (Practical examples 15 and 16 in Table 1).

In order to improve treatment capability (treatment capacity) in surface modification for the fluororesin film, with the ion irradiator 2 held in position, while paying the fluororesin film out from one of resin spools attached to a roll and winding the fluororesin film on the other one of resin spools attached to a roll, a certain region of the fluororesin film between the pay-out spool and the take-up spool is irradiated with an ion beam.

Figure 7:
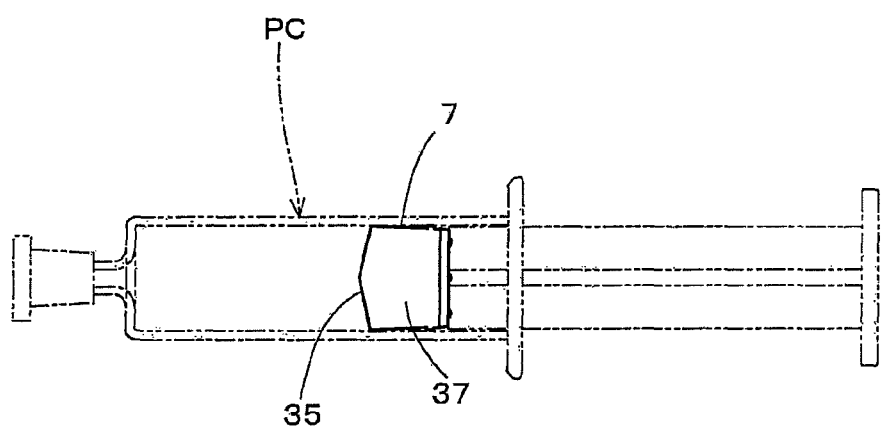
FIG. 7 is a diagram showing a medical rubber product applied to a pre-filled syringe.
Figure 8:
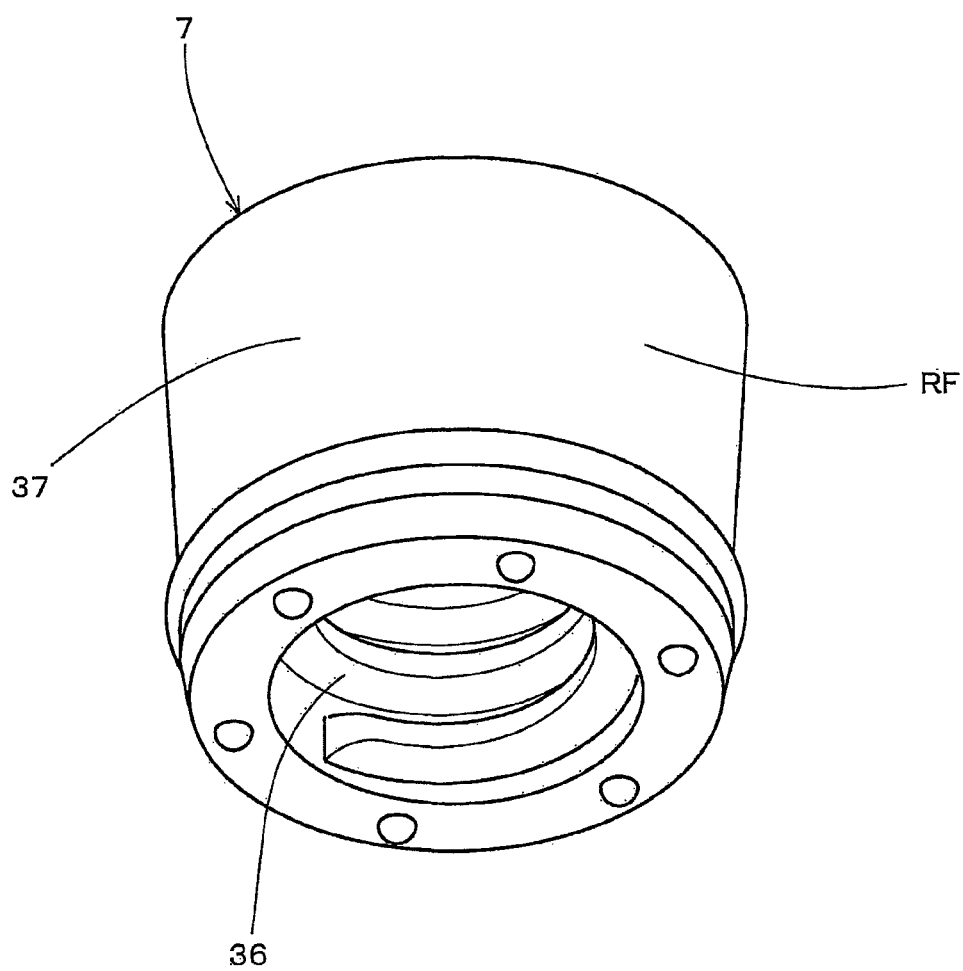
FIG. 8 is a perspective view of the medical rubber product.
Figure 9:
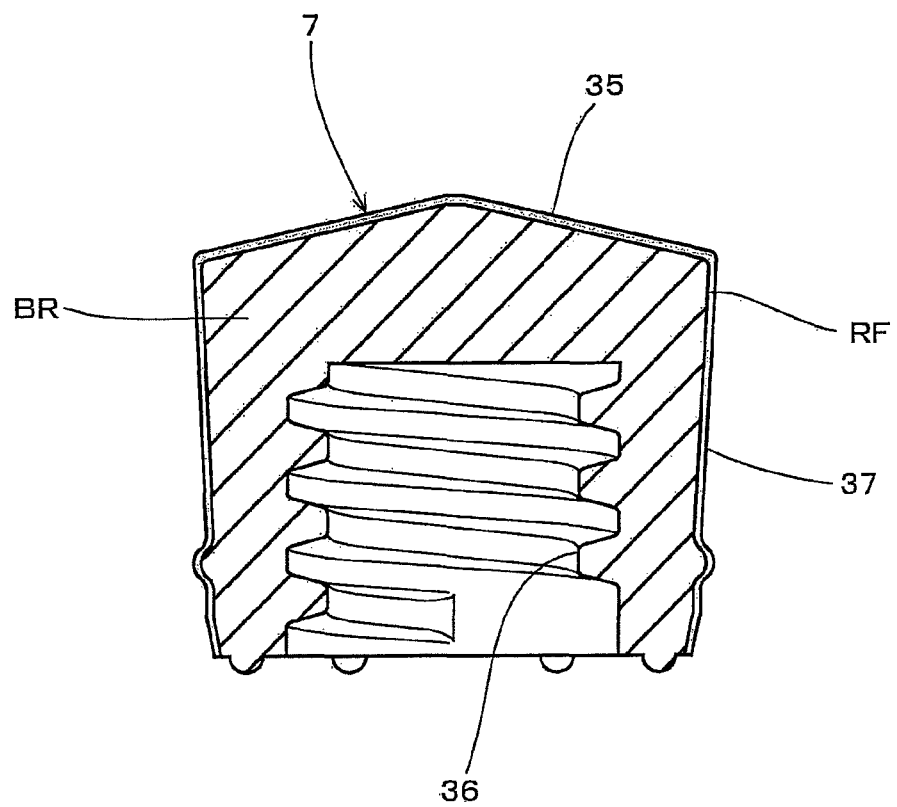
FIG. 9 is a sectional view of the medical rubber product.

FIG. 7 is a diagram showing a medical rubber product applied to a pre-filled syringe PC, FIG. 8 is a perspective view of the medical rubber product, and FIG. 9 is a sectional view of the medical rubber product.

The medical rubber product shown in FIGS. 7 to 9 has the form of a piston 7 for pushing liquid drug preparations contained in the pre-filled syringe PC out. Referring to FIGS. 8 and 9, the piston 7 has a substantially cylindrical shape, and one of its opposite end faces (bottom surface) is shaped into a beveled pressing surface 35 (a circumferential part of which is defined by a frustum of circular cone whose height is very small relative to the diameter of the bottom surface). The piston 7 is opened at the other end face, with an axially disposed internal thread 36 brought into view. The piston 7 is produced by bonding a fluororesin film (PTFE film) having its surface roughened by the surface-modifying apparatus 1 and butyl rubber together through vulcanization adhesion. Thus, the most part of the piston 7 is made of the butyl rubber BR, and the fluororesin film RF bonded to the butyl rubber BR is exposed at the pressing surface 35 and the periphery 37 of the piston 7.

In the piston 7, the surfaces of the pressing surface 35 and the periphery 37 are formed of the fluororesin film RF. Therefore, neither changes in quality or degeneration of liquid drug preparations contained in the pre-filled syringe PC nor changes in quality or degeneration of the piston 7 in itself will take place. Moreover, that surface of the piston 7 which slides over the cylinder surface is made of fluororesin having a self-lubricating nature. This makes it possible to achieve smooth injection of liquid drug preparations by the pre-filled syringe PC.

The rubber composite composed of the fluororesin film RF and the rubber bonded together is applicable to, in addition to the piston 7 of the pre-filled syringe PC, other various rubber products for medical use, including a stopper of a bottle for a chemical in liquid form.

The application of the rubber composite is not limited to medical purposes, and it can therefore find a wide range of applications that necessitate the elasticity of rubber, the self-lubricating nature of fluororesin, chemical resistance, heat resistance, etc. For example, the rubber composite is applicable to a gasket for industrial equipment.

In the embodiments as above described, there is no particular limitation to the shape of fluororesin. In the case of bonding fluororesin to rubber through vulcanization adhesion while shaping it into a solid body of certain shape, it is possible to use fluororesin which has been molded into that shape in advance. Moreover, in the case of using fluororesin in the form of a thin film, it is possible to mold the fluororesin together with rubber simultaneously in the course of vulcanization adhesion. The latter alternative is desirable from the standpoint of manufacturing process steps. In this case, although it is preferable that the film has as small a thickness as possible to attain better moldability, the film having too small a thickness is susceptible to development of pinholes resulting for example from a stretch by deformation. While the film is preferably made to have a thickness in a 0.044 mm- to 0.15 mm range, the thickness can be changed on an as needed basis in consideration of the amount of deformation.

It is preferable that the average energy of the ions of an ion beam for irradiation falls within the range of 0.8 keV to 2.5 keV. If the energy level is low, undesirably, much time will be required for treatment operation. If the energy level is high, undesirably, fluororesin will be heavily decomposed with a consequent reduction in vacuum due to a degassing phenomenon (gas from decomposed resin). A particularly desirable energy range is from 1.2 keV to 1.8 keV.

In an anode layer ion source, one widely held view is that the average energy imparted to ions is equal to about one-half of the value of voltage impressed on an ion source. According to this common knowledge, a setting voltage range for the provision of that energy is from 1.6 kV to 5.0 kV insofar as the average energy falls within the range of 0.8 keV to 2.5 keV, or from 2.4 kV to 3.6 kV insofar as the average energy falls within the range of 1.2 keV to 1.8 keV.

While the number of ions per unit area for irradiation to the fluororesin film is so selected as to attain the intended adhesion strength, preferably it falls within the range of $10^{13}/cm^2$ to $10^{18}/cm^2$. If the number is less than $10^{13}/cm^2$, the required surface modification effect cannot be obtained with a consequent decrease in adhesion strength. If the number is greater than $10^{18}/cm^2$, a modified surface layer will be decomposed even further with a consequent impairment in efficiency. When effecting ion irradiation, it is possible to cause the ejection of a necessary amount of ions at one time, or it is also possible to repeat the ejection of a small amount of ions a given number of times until the intended total number of ions is reached. For the sake of avoiding thermal damage to fluororesin, it is desirable to repeat ion irradiation with ejection of a small number of ions on each occasion a given number of times.

Otherwise, the overall design, the configuration, the dimension, the number, the material, and so forth as to the surface-modifying apparatus 1 and the constituent components thereof can be changed on an as needed basis within the scope and spirit of the present invention.

Industrial Applicability

The present invention is applicable to a surface-modified fluororesin film, a rubber composite formed by bonding the fluororesin film and rubber together, and a medical rubber product made of the rubber composite.

Explanation of Reference Symbols

2 Ion irradiator (Anode layer ion source)
7 Piston (Medical rubber product)
BR Butyl rubber (Rubber)
RF Fluororesin film

The invention claimed is:

1. A method for manufacturing a surface-modified fluororesin film comprising the step of:
    performing surface roughening on a fluororesin film by applying an ion beam at an irradiation voltage of 1.5 kV or more and 3.5 kV or less from an anode layer ion source to a surface of said fluororesin film.

2. The method for manufacturing the surface-modified fluororesin film according to claim 1,
    wherein said fluororesin film is made of any one of PTFE, denatured PTFE, PFA, and ETFE.

3. A method for manufacturing a rubber composite comprising the steps of:
    performing surface roughening on a fluororesin film by applying an ion beam at an irradiation voltage of 1.5 kV or more and 3.5 kV or less from an anode layer ion source to a surface of said fluororesin film; and
    placing a rubber over said surface of said fluororesin film and bonding them together by means of vulcanization molding.

4. A rubber product comprising:
a fluororesin film; and
a rubber,
said fluororesin film having its surface roughened by irradiation of an ion beam at an irradiation voltage of 1.5 kV or more and 3.5 kV or less from an anode layer ion source,
wherein said rubber is placed over the roughened surface of said fluororesin film, and, through a vulcanization molding process, said rubber finds its way into the roughened surface of said fluororesin film so as to adhere tightly to said fluororesin film under an anchor effect.

* * * * *